United States Patent [19]
Mortier et al.

[11] Patent Number: 5,372,144
[45] Date of Patent: Dec. 13, 1994

[54] NAVIGABILITY IMPROVED GUIDEWIRE CONSTRUCTION AND METHOD OF USING SAME

[75] Inventors: Todd Mortier, Minneapolis; Charles Euteneuer, St. Michael; Cyril Schweich, Jr., St. Paul, all of Minn.

[73] Assignee: SciMed Life Systems, Inc., Minneapolis, Minn.

[21] Appl. No.: 983,648

[22] Filed: Dec. 1, 1992

[51] Int. Cl.⁵ .............................................. A61B 5/02
[52] U.S. Cl. .................................................. 128/772
[58] Field of Search .............. 128/657, 772; 604/95, 604/164, 280-283

[56] References Cited

U.S. PATENT DOCUMENTS 4,966,163 10/1990 Kraus et al. ..................... 128/772

FOREIGN PATENT DOCUMENTS

WO92/19311 11/1992 WIPO .

*Primary Examiner*—Max Hindenburg
*Attorney, Agent, or Firm*—Nawrocki, Rooney & Silvertson

[57] ABSTRACT

A medical guidewire includes a distal end for entering and navigating in a lumen. The distal end comprises a core having a length for navigating the guidewire in the lumen. A formable distal tip is included at the distal end of the core, and a sleeve element substantially surrounds the core over less than a majority of the length of the core. The sleeve element is rotatable with respect to the core, and is offset proximally of the formable distal tip such that the formable distal tip is movable independently of the sleeve element. The sleeve element is positively coupled to the core such that the sleeve element and the core move substantially conjointly axially within the lumen. An improvement for improving navigability of a medical guidewire in a lumen is also provided. The improvement comprises a sleeve element separate from and disposed around the core. The sleeve element is rotatable with respect to the core. Multiple sleeve elements may be provided on a single core. Further provided is a method of navigating a medical guidewire within a lumen having an interior surface. The method generally comprises the steps of: providing a medical guidewire having a core for navigating the guidewire within the lumen and a sleeve element surrounding the core and being rotatable with respect to the core; engaging the sleeve element with the interior surface; and rotating the core with respect to the sleeve element for navigating the guidewire within the lumen. The method also provides for effective decoupling of axial and rotational movements of the guidewire.

19 Claims, 4 Drawing Sheets

NAVIGABILITY IMPROVED GUIDEWIRE CONSTRUCTION AND METHOD OF USING SAME

BACKGROUND OF THE INVENTION

The present invention relates generally to a novel device for navigating in narrow, tortuous passageways, such as vascular systems, catheter lumens, and the like, and a method of using the device. More specifically, the invention relates to a novel construction of a medical guidewire and to novel improvements incorporated in a medical guidewire that facilitate the navigability thereof. An improved method of navigability of a guidewire within a lumen is also provided.

Given the increased popularity of non-invasive medical procedures, such as angioplasty and the like, the need for and use of medical guidewires has correspondingly increased. Medical guidewires are used to navigate through narrow, tortuous passageways within a patient in order to reach and to guide appropriate medical instruments, devices, and treatments to a desired treatment site within the patient's body. To do this, the guidewire is inserted into the patient's body through a small access, such as an incision or puncture opening and into the patient's vascular system. The guidewire is progressively fed into the patient's body in an attempt to reach the desired treatment site, while the progression of the wire is monitored by a treating physician, clinician, or other medical professional through appropriate means, such as radiography and the like. In some cases, the medical guidewire may be inserted into and navigated through a catheter lumen, thereby guiding the catheter to an intravascular treatment site.

Because the desired treatment site may be difficult to reach, the guidewire must often be rotated or otherwise steered by the physician as the guidewire is inserted into the patient's body. The physician applies forces to the proximal, out-of-body end of the guidewire hoping that the distal, in-body end of the wire will be influenced to proceed in the desired direction. These proximally applied forces may be rotational forces, axial forces, or forces having other directions to facilitate intravascular navigation of the wire. Specifically, the physician applies forces to the proximal end of the wire which cause the distal end thereof to rotate in a particular direction. In addition, the distal end of the wire may be provided with a coil or tip having a predetermined, preformed curvature which may facilitate steering of the guidewire within the patient's body.

This steering, however, can become quite complex and tedious depending upon location of the treatment site. For instance, if the treatment site is located generally within or proximate to a soft tissue organ, such as the liver, or within the cerebral vasculature, the guidewire may have to be navigated around a number of bends in the patient's vascular system if the treatment site is to be reached. Also, the guidewire may have to be directed into proper branches of the vascular system when the guidewire reaches a juncture of multiple vessels or lumens. By deforming the distal end into a particular configuration, such as a "J"-shape, the treating physician may be able to select an appropriate vascular branch by properly rotating the proximal portion of the guidewire. Rotation of the proximal end induces rotation of the distal end of the guidewire, thereby directing a distal end of the preformed "J" into or towards the proper vascular branch. Once the distal end of the "J" has entered the desired branch, proper application of axial and rotational forces to the proximal end can cause the distal end, and thus, a requisite axial length of the guidewire, to move within the vascular system towards the intended treatment site. But, for this steering method to work, the treating physician must be able to rotate the distal end of the guidewire, and the easier the rotation of the distal end, the easier the procedure progresses.

As the guidewire is navigated around and through an ever increasing number of bends, branches and curves, the contact between the guidewire and an interior surface of the patient's vascular system or an interior surface of a catheter lumen generates friction therebetween, which creates a correspondingly increasing torque or navigation-inhibiting resultant force acting upon the guidewire. Specifically, the contact between the outer surface of the guidewire and a particular lumen interior surface can prevent or resist rotation, often necessary for intravascular navigation, of the guidewire responsive to rotational forces proximally applied by a treating physician. As this resultant force increases, the guidewire becomes progressively more difficult to navigate because of the resistance to steering force transmission along the axial length of the guidewire. Thus, the rotation of the distal end may lag behind corresponding rotation of the proximal end.

Furthermore, if the distal end of the guidewire is curved, or preformed into a "J", the guidewire often must be rotated in order to direct the curved end around a bend or into a desired branch lumen. However, the resultant force on the guidewire, and especially on the distal end, may limit significantly the physician's ability to rotate or maneuver the guidewire, thereby complicating the procedure. Similar steering difficulties can be encountered when the guidewire is located within a catheter lumen within the patient's vascular system. Navigability of the guidewire may also be limited because portions of the distal end of the guidewire have different lubricity, viz. some portions of the guidewire may slide within the vascular or catheter lumen more readily than others.

Many guidewires are provided with flexible coils on the distal ends thereof to improve navigability or pushability of the guidewires in narrow passageways without greatly increasing the stiffness of the wire. But, these coils may kink, thereby inhibiting guidewire navigability. To further improve navigability, some of these coils are coated or overmolded with a lubricous substance. However, coating or overmolding the coils can lock adjacent coils together. Once these coils are interlocked, the range of flexibility thereof, as a whole, may be limited, thereby inhibiting navigability of the guidewires.

These various effects, either alone or in conjunction, can significantly decrease the guidewire's navigability within the vascular or catheter lumen. This decreased navigability of the guidewire may complicate the endovascular procedure being attempted and may limit treatment site accessibility. Accordingly, the present invention provides a novel guidewire structure which solves many, if not all of the above-discussed problems encountered with steering or navigating guidewires within a patient's vascular system or other lumen. The invention also provides a novel sleeve element that can be used to improve the navigability of guidewires, thereby increasing treatment site accessibility. The invention further provides a novel guidewire construction with a distal end having substantially constant lubricity. The invention also provides a lubricous, flexible sheath, separate from a distal end coil, for encompassing the coil, for improving navigability of the guidewire. Furthermore, a novel method of guidewire navigation is also provided.

SUMMARY OF THE INVENTION

A general object of the invention is to provide a novel device for increasing navigability of narrow, tortuous passageways, such as vascular systems and the like.

A more specific object of the present invention is to provide a novel guidewire having increased maneuverability within a vascular system.

Another object of the invention is to provide a guidewire having particular utility in navigating to and within complex or highly tortuous vasculature.

An additional object of the present invention is to provide a novel guidewire having means for shielding a distal end thereof from navigation-inhibiting forces.

A further object of the invention is to provide a novel sleeve element provided as part of a medical guidewire construction which can increase maneuverability of the guidewire in a narrow, tortuous lumen system.

Another object of the present invention is to provide a novel guidewire structure which can increase treatment site accessibility.

A further object of the invention is to provide a novel guidewire construction which substantially decouples rotational movement of the core wire from axial movement of the guidewire and from forces exerted on the sleeve element.

Another object of the invention is to provide a guidewire that is more resilient, per a given stiffness of the wire, than currently available wires.

An additional object of the present invention is to provide a novel method of navigating a guidewire in a lumen.

A further object of the invention is to provide a novel guidewire construction having an increased ability to select desired branch lumens in a patient's vascular system.

A novel medical guidewire, constructed according to the teachings of the present invention, includes a distal end for entering and navigating in a lumen. The distal end comprises a core having a length for navigating the guidewire in the lumen. A formable distal tip is included at the distal end of the core, and a sleeve element substantially surrounds the core over less than a majority of the length of the core. The sleeve element is rotatable with respect to the core, and is offset proximally of the formable distal tip such that the formable distal tip is movable independently of the sleeve element. The sleeve element is positively coupled to the core such that the sleeve element and the core move substantially conjointly axially within the lumen. An improvement for facilitating navigability of a medical guidewire in a lumen is also provided. The improvement comprises a sleeve element separate from and disposed around said core. The sleeve element is rotatable with respect to the core. Multiple sleeve elements may be provided on a single core. Further provided is a method of navigating a medical guidewire within a lumen having an interior surface. The method generally comprises the steps of: providing a medical guidewire having a core for navigating the guidewire within the lumen and a sleeve element surrounding the core and being rotatable with respect to the core; engaging the sleeve element with the interior surface; and rotating the core with respect to the sleeve element for navigating the guidewire within the lumen. The method also provides for effective decoupling of axial and rotational movements of the guidewire.

BRIEF DESCRIPTION OF THE DRAWINGS

The organization and manner of the structure and operation of the invention, together with further objects and advantages thereof, may best be understood by reference to the following description taken in connection with the accompanying drawings, wherein like reference numerals identify like elements in which.

DETAILED DESCRIPTION OF PREFERRED EMBODIMENTS

While the invention may be susceptible to embodiment in different forms, there are shown in the drawings, and herein will be described in detail, specific embodiments with the understanding that the present disclosure is to be considered an exemplification of the principles of the invention, and is not intended to limit the invention to that as illustrated and described herein.

Figure 1:
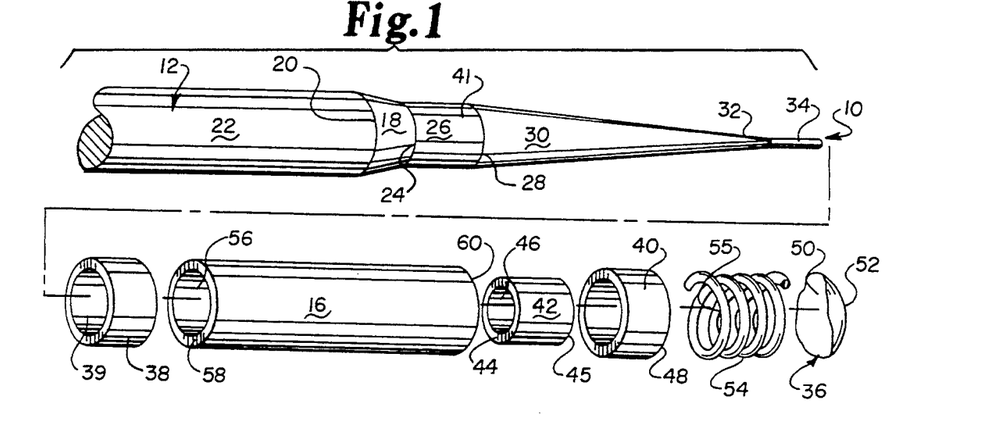
FIG. 1 is an exploded perspective view of a distal end of a guidewire, constructed according to the teachings of the present invention, having a sleeve element for improving navigability of the guidewire.
Figure 2:
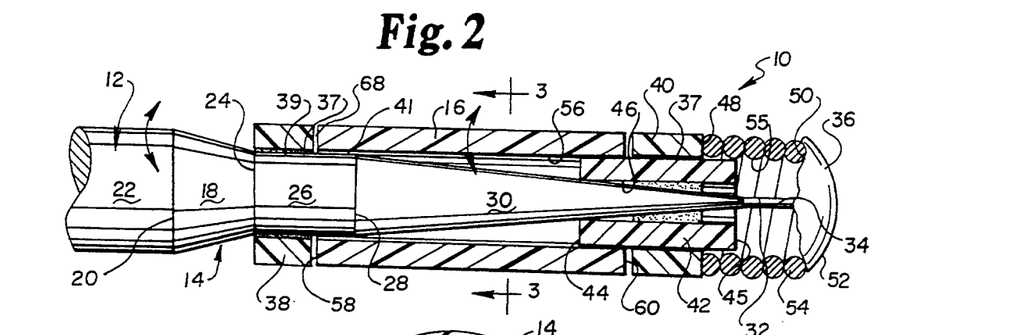
FIG. 2 is a partially sectioned side elevational view of the sleeve element of FIG. 1 disposed on a distal end of the guidewire of FIG. 1.

Referring initially to FIG. 1, a distal end 10 of a guidewire 12, constructed according to the teachings of the present invention, is illustrated in exploded perspective form. As shown in FIGS. 1 and 2, the distal end 10 of the guidewire 12 generally comprises a core wire 14 for navigating the guidewire 12 within a lumen, such as a blood vessel, catheter lumen, and the like, having novel means for increasing the navigability of the guidewire 12 in the form of a substantially cylindrical sleeve element 16 substantially surrounding and moveable or rotatable substantially independent of the core wire 14. Conversely, it can be stated that the core wire 14 is moveable or rotatable substantially independent of the sleeve element 16, depending upon chosen reference frame. It is to be noted that the sleeve element 16 is separate from and independent of the core wire 14, and is preferably spaced radially from the core wire 14 a distance sufficient for allowing substantially independent movement of the sleeve element 16 with respect to the core wire 14. The sleeve element 16 is also positively coupled to the core wire 14 such that the sleeve element 16 and the core wire 14 move substantially conjointly axially within a vascular of catheter lumen. As will be discussed in greater detail below, the sleeve element 16 comprises means for increasing navigability of the guidewire 12 while also shielding the core wire 14 from navigation-inhibiting resultant forces, generated by contact of the guidewire 12 with an interior surface of the lumen, applied to the distal end 10. The sleeve element 16 allows the guidewire 12 to more easily select, as compared to some prior art guidewires, a desired branch lumen in a patient's vascular system. This is due, in part, to the fact that the sleeve element 16 effectively decouples the rotational movement of the core wire 14 from the forces exerted on the sleeve element 16. This also effectively decouples rotational and axial movement of the guidewire 12. Specifically, as the guidewire 12, or, more precisely, the core wire 14 is rotated to navigate the guidewire 12 in vasculature, the sleeve element 16 does not conjointly rotate. However, when the guidewire 12 is advanced axially within vasculature, both the core wire 14 and the sleeve element 16 move conjointly.

The core 14 of the guidewire 12 may be a braid, a tube, or other suitable structure, and includes a frusto-conical or tapered segment 18 connected at a relatively larger diameter end 20 thereof to a length 22 of the wire 12, only a portion of which is visible in the Figures, having a suitable diameter for insertion into a patient's vascular system or other lumen. The tapered segment 18 also includes a relatively smaller diameter end 24, opposite to the end 20, which is connected to a constant diameter segment 26. The segment 26 has a diameter smaller than the diameter of the length 22 of the core 14. A suitable portion, preferably including the proximal portion, of the length 22 is coated with a lubricous substance, such as a fluoropolymer and the like, to reduce friction on the guidewire 12 as it is advanced through a particular lumen. This coating can also reduce navigation-inhibiting forces when the core wire 14 is rotated within the lumen. This coating can also facilitate intravascular navigation of the guidewire 12, as well as axial progression of the wire 12 within the lumen. As will be discussed in greater detail later, the sleeve element 16 may also be similarly coated, thereby aiding in intravascular axial movement thereof.

An end 28 of the segment 26, opposite to the end 24, is connected to a relatively elongate frusto-conical or tapered segment 30 defining a gradually decreasing diameter. An end 32 of the segment 30 opposite to the end thereof connected to the segment 26 is connected to a formable distal segment 34 having dimensions substantially smaller than corresponding dimensions of the segment 26. The segment 34 is preferably flattened or stamped, thereby giving it a substantially rectangular cross-section. In some cases, the segment 34 can be a safety ribbon. Thus, the core wire can comprise a single piece, or, alternatively, may comprise a plurality of joined pieces.

An end 36 of the segment 34, opposite to the end thereof connected to the segment 30, is connected to a substantially rounded distal end tip 36, the significance of which will be discussed later. The end tip 36 is formed by a suitable welding process, and defines a diameter substantially equal to the diameter defined by the relatively large diameter end 20 and the length 22 so that the distal end 10 presents a relatively smooth external profile.

Figures 3, 4:
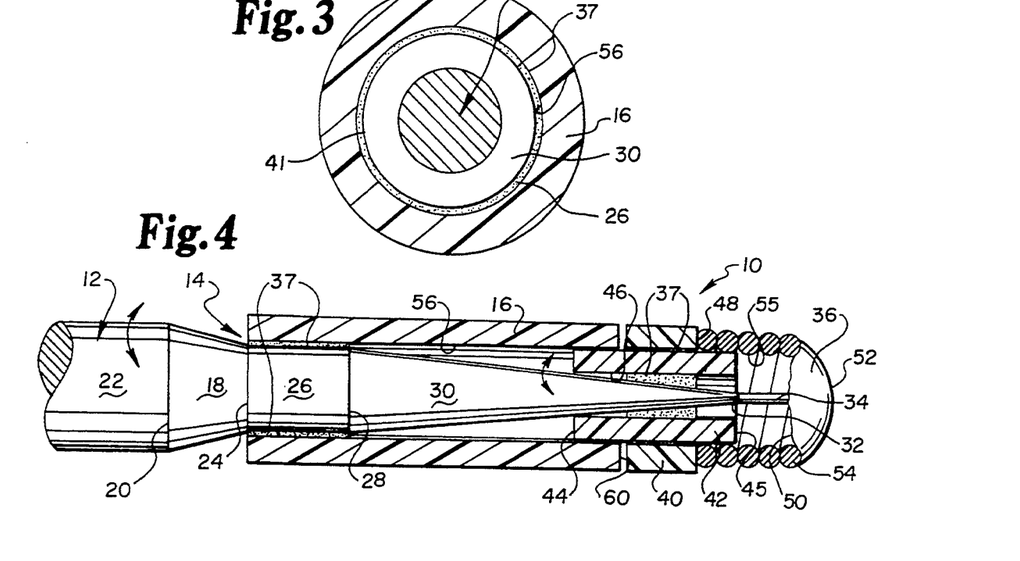
FIG. 3 is a sectional view taken along line 3—3 of FIG. 2.
FIG. 4 is a partially sectioned side elevational view, similar to that of FIG. 2, of another embodiment of the present invention, having a proximal end of the sleeve element attached to the guidewire.

In the embodiment of the invention illustrated in FIGS. 2 and 3, a proximal retaining or positively coupling member or annulus 38, having an inner diameter somewhat larger than the diameter defined by the segment 26, is fixedly attached, along its inner diameter surface 39, preferably to the constant diameter segment 26 by suitable means 37, such as an adhesive and the like. The annulus 38 preferably does not extend along the entire axial length of the segment 26. As will be discussed further below, this allows a portion of the segment 26 to act as a bearing surface 41 for the sleeve element 16. In this manner, the annulus 38 can positively locate the sleeve element 16 on the core 14 of the guidewire 12 while allowing the sleeve element 16 to rotate independently of and with respect to the core 14.

A distal retaining or positive coupling member or annulus 40, having an inner diameter substantially equal to the inner diameter of the annulus 38, is fixedly attached to the tapered segment 30 adjacent the end 32 of the segment 30. However, because the diameter defined by the tapered segment 30 adjacent the end 32 is substantially smaller than the diameter defined by the constant diameter segment 26, a bearing 42 should be utilized in order to properly mount the annulus 40 to the tapered segment 30. In this way, the annuluses 38 and 40 cooperate to positively locate and maintain the sleeve element 16 about the core wire 14.

Specifically, the bearing 42 comprises a substantially cylindrical body or hypotube defining a constant inner diameter larger than the diameter defined by the tapered segment 30 adjacent the end 32. The particular bearing 42 illustrated in FIG. 2 comprises a cylinder of polymeric material, but other suitable materials can be used. But, because the diameter defined by the tapered segment 30 gradually increases as one progresses therealong from the end 32 towards the end 28, the inner diameter of the bearing 42 is chosen so that a proximal end 44 of the bearing 42 engages the outer surface of the tapered segment 30, as shown in FIG. 2. This insures that the axes of elongation of the bearing 42 and the annulus 40 will be parallel to the corresponding axes of the core 14 and the annulus 38. Thus, the bearing 42 provides a bearing surface for the sleeve element 16 in much the same manner as the constant diameter segment 26 does, and facilitates rotation of the sleeve element 16 substantially independent of the core wire 14.

The bearing 42 is fixedly attached, along its inner diameter surface 46, to the tapered segment 30 adjacent the end 32 by appropriate means 37, such as an adhesive and the like. Because the proximal end 44 of the bearing 42 engages the outer surface of the tapered segment 30, the bearing 42 may also be force fitted onto the tapered segment 30. The distal annulus 40 is attached, along its inner diameter surface 48, by similar means 37 to an outer diameter surface of the bearing 42. It is to be noted that axial lengths and relative dispositions of the annulus 40 and the bearing 42 are predetermined such that distal ends of the annulus 40 and the bearing 42 do not align, as shown in FIG. 2.

The distal end of the annulus 40 forms a coil engaging surface 48. The coil engaging surface 48 cooperates with a suitable coil engaging surface 50 or proximal portion formed by the end tip 36, opposite to a rounded surface 52 thereof, to locate a coil 54 therebetween in well known fashion. The end tip 36 may be formed by welding or soldering such that the tip 36 binds a few adjacent coils comprising the coil 54. The coil 54 is not compressed between the surfaces 48 and 50. The coil 54 preferably defines an outer diameter substantially equal to the outer diameters of the sleeve element 16 and the annuluses 38 and 40 so that the distal end 10 presents a substantially smooth profile. Also, in a preferred construction, the coil 54 comprises a radiopaque material, such as platinum or the like, for allowing an operating physician to monitor progression of the guidewire 12 within a lumen by radiography.

The dimensions of the portions of the tapered segment 30 beyond the coil engaging surface 48 and the segment or ribbon 34 can be chosen so that any desired suitable construction of coil 54 can be utilized with the guidewire 12. Also, the distal end of the tapered segment 30 and the segment or ribbon 34 may be bent or formed by a physician into any desired configuration, such as a "J", for facilitating maneuverability and selectability of the guidewire 12.

Because the coil 54 flexes along with the distal end of the segment 30 and the segment 34, the coil 54 may kink as it flexes. In order to prevent kinking of the coil 54 adjacent the coil engaging surface 48, and to strengthen the connection between the distal end 10 and the coil 54, a distal end 45 of the bearing 42 projects beyond the coil engaging surface 48 into the interior of the coil 54. The bearing 42 also provides a smooth transition of flexibility from the sleeve element 16 to the coil 54. The dimensions of the bearing 42 and the coil 54 are chosen such that an interior diameter surface 55 of the coil 54 supportively contacts an outer diameter surface of the bearing 42, as shown in FIGS. 2 and 4.

The sleeve element 16 is a hollow substantially cylindrical body, preferably having an inner diameter substantially equal to the inner diameters of the annuluses 38 and 40, and the outer diameter of the bearing 42. The sleeve element 16 also has an outer diameter substantially equal to the outer diameters of the annuluses 38 and 40 so that the sleeve element 16 and the annuluses 38 and 40 present a substantially smooth, even outer surface defined by their respective outer diameters. This may be important to minimize the possibility of injury to the patient or damage to a catheter or the guidewire 12 as contact occurs between this outer surface of the sleeve element 16 and the interior of a particular lumen. Further, by presenting a substantially constant, even outer surface profile from the distal end of the annulus 40 to the proximal end of the annulus 38, the lubricity of the outer surface as a whole may be made substantially constant by appropriate choice of materials and coatings. Also, by presenting such an outer surface profile, a lubricous coating, such as a hydrophilic material and the like, can be applied to the entire outer surface, thereby further increasing navigability of the guidewire 12. More importantly, the sleeve element 16 is coated to reduce any friction, i.e. resultant force, generated between the guidewire 12 and a particular lumen into which the guidewire 12 is inserted. This facilitates axial shifting of the guidewire 12 within the lumen.

When assembled, the core wire 14 extends through the interior of the sleeve element 16 with the sleeve element 16 being rotatably trapped between the annuluses 38 and 40. The dimensions of the sleeve element 16 may be chosen such that the sleeve element 16 is slightly spaced axially from the distal and proximate ends, respectively, of the annuluses 38 and 40 to allow for variances which may occur due to curvature of the core wire 14 within the sleeve element 16. Such variances may bring the sleeve element 16 into contact with the annuluses 38 or 40, which contact might inhibit rotation of the sleeve element 16 about the core wire 14. However, this axial spacing is quite small, within the range of 0.1 mm to 3 mm, so that the navigation of the guidewire 12 will not be compromised.

Portions of an inner diameter surface 56 of the sleeve element 16 rotatably rest upon the constant diameter segment 26 and the outer diameter surface of the bearing 42. It is to be noted that the sleeve element 16 is not attached to or mounted on the core wire 14 in any way. This allows the sleeve member 16 to rotate with respect to the core wire 14, or, viewed from another reference frame, allows the core wire 14 to rotate with respect to the sleeve element 16. Because the guidewire 12 and the core 14 are capable of rotation substantially independent of the sleeve element 16, the sleeve element 16 comprises means for increasing navigability of the guidewire 12 and treatment site accessibility while also shielding the distal end 10 and the core wire 14 from resultant forces, as will be discussed in greater detail later. Specifically, any resultant force generated by contact between the sleeve element 16 and a portion of a vascular or catheter lumen will not be transmitted to the core wire 14 and thereby to the guidewire 12. Thus, the resultant force on the sleeve element 16 will not inhibit steering, manipulation, selectability or maneuverability of the distal end 10 of the guidewire 12.

Another embodiment of the invention is illustrated in FIG. 4. This embodiment of the invention is substantially similar to the above-described embodiment, as is indicated by the like reference numerals. Accordingly, this alternative embodiment differs from the first-discussed embodiment only to the extent of the differences discussed in the following paragraphs. This embodiment lacks the proximal annulus 38. The particular bearing 42 illustrated in FIG. 4 is a metal hypotube, however, it is to be understood that a polymeric cylinder bearing, for example, such as that illustrated in FIG. 2, can also be used.

Specifically, as shown in FIG. 4, the sleeve element 16 is fixedly attached, at its proximal end 58, to the bearing surface 41 of the constant diameter segment 26 by means 37. However, it is to be noted that a distal end 60 of the sleeve element 16 is not attached to the core wire 14. In this embodiment, the sleeve element 16 is also able to increase navigability and selectability of the guidewire 12 and accessibility of a particular treatment site and also to substantially shield the distal end 10 and the core wire 14 from forces because a distal portion of the core wire 14 can rotate substantially independently of and with respect to the distal end 60 of the same element 16.

In the preferred construction, the portion of the constant diameter segment 26 to which the proximal end 58 of the sleeve element 16 is attached has a moment of inertia that is substantially larger than a corresponding moment of inertia of a portion of the core wire 14 adjacent the distal end 60 of the sleeve element 16. Because the sleeve element 16 is attached to a portion of the core wire 14 having a relatively large moment of inertia, resultant force generated by contact of the sleeve element 16 with a lumen can be transmitted to that relatively large moment of inertia portion of the core 14. By transmitting the generated resultant force to the relatively large moment of inertia portion in this manner, the force does not significantly inhibit navigability of the distal end 10 of the guidewire 12 within the patient's vascular system. Additionally, because the distal end 60 of the sleeve element 16 is not attached to the core wire 14 and, specifically, not to the tapered segment 30 thereof, resultant force applied to the sleeve element 16 is not transmitted to the tapered segment 30, the segment or ribbon 34, or the coil 54. Thus, the navigability of the guidewire 12 is not reduced by the forces applied to the sleeve element 16, thereby making treatment sites, especially those located proximate to or within a soft tissue organ or intracranial vasculature for example, relatively more accessible.

It is to be understood, however, that it is not necessary to have a relatively large moment of inertia portion and a relatively small moment of inertia portion, or even a tapered segment 30 on the core wire 14 for the sleeve element 16 to function as described. By fixing the proximal end 58 of the sleeve element 16 to a relatively proximal portion of the core wire 14, and leaving the distal end 60 of the sleeve element 16 unattached, a relatively distal portion of the core wire 14 is able to flex and rotate substantially free of the inhibiting effects of the resultant forces applied to the sleeve element 16. The sleeve element 16, in both the embodiments of FIG. 2 and FIG. 4, effectively shields the core wire 14, or at least distal portions thereof, from navigation-inhibiting forces, thereby increasing the navigability of the guidewire 12.

In some guidewire constructions, an outer surface thereof may have crevices or spaces along its axial length into which bodily fluids, such as blood and the like, can flow or collect. The fluids can thicken or coagulate in the spaces. When sufficient fluid has collected or coagulated in the spaces on the guidewire, the portion thereof including those spaces may become relatively more rigid. The relatively increased rigidity of those portions can limit the flexibility or steerability of the guidewire. Thus, collection and/or coagulation of such fluids can decrease the navigability of the guidewire within a lumen.

The spaces on the guidewire may also "catch" or "pinch" a portion of the interior surface of a lumen as the guidewire is navigated therethrough. Specifically, the guidewire may be rotated such that a portion of the lumen interior surface is disposed within a space. When the guidewire is subsequently rotated, the rotation may decrease the dimensions of the space, thereby clamping or compressing the lumen interior surface portion against adjacent boundaries of the space. This catching can limit navigability of the guidewire because of the increased resistance to guidewire rotation and axial progression generated by the clamping of the lumen interior surface. Also, the boundaries of the spaces may contact the interior surface of a lumen, thereby generating increased navigation-inhibiting friction between the guidewire and the lumen.

Figure 5:
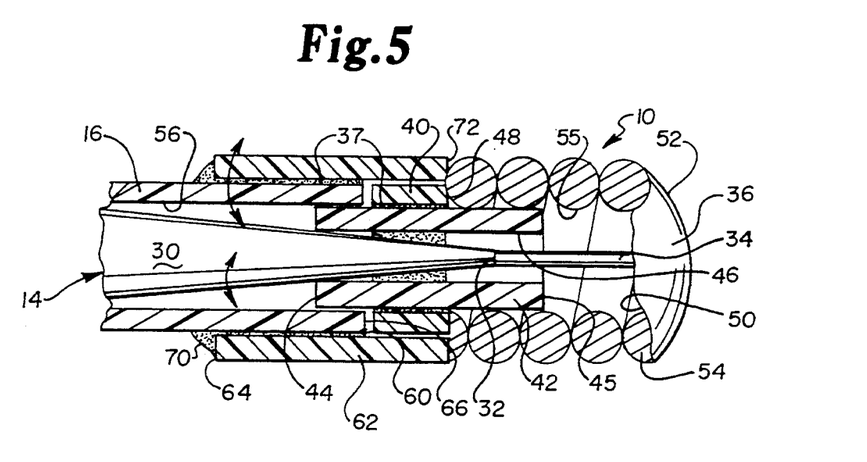
FIG. 5 is a partially section side elevational view of yet another embodiment of the invention utilizing a sleeve element and an annulus.

FIG. 5 shows yet another embodiment of the invention. The embodiment of FIG. 5 is substantially similar to the embodiments illustrated in FIGS. 1 through 4, as is indicated by the like reference numerals, except for the differences to be discussed hereinbelow. Specifically, this embodiment utilizes an additional annulus 62 surrounding the distal end 60 of the sleeve element 16. This additional annulus 62 is employed to give the distal end 10 a smoother external profile, thereby reducing the probability that the distal end 10 will "catch" on a portion of the lumen, and to eliminate spaces or crevices into which navigation-inhibiting fluids, such as blood, can flow and coagulate. While the annulus 62 is shown surrounding only the distal end 60 of the sleeve element 16, it is envisioned that a similar annulus may also be provided surrounding the proximal end 58 of the sleeve element 16 as well. This aspect of the invention may be of particular importance when the guidewire 12 is inserted directly into a patient's blood vessel.

The annulus 62 is a substantially hollow cylindrical body whose dimensions are predetermined such that the annulus 62 defines an inner diameter larger than the outer diameters defined by the sleeve element 16 and the annulus 40, and defines an outer diameter substantially equal to The outer diameter of the coil 54. In this manner, the annulus 62 can surround the sleeve element 16 and the annulus 40, and will not inhibit or interfere with the substantially independent rotation of the sleeve element 16. Also, the annulus 62 cooperates with the outer diameter surface of the coil 54 to form a substantially smooth, continuous outer surface profile from the end tip 36 to a proximal end 64 of the annulus 62.

The axial dimension of the annulus 62 is sufficient so that the annulus 62 extends towards the length 22 from a plane defined by the coil engaging surface 48 a distance sufficient to cover an annular space 66 formed between the distal end 60 of the sleeve element 16 and the proximal end of the annulus 40. Because the annular space 66 is covered by the annulus 62, the distal end 10 is positively prohibited from catching a portion of an interior surface of a lumen into which the guidewire 12 is inserted. This improves the navigability of the guidewire 12. If a similar annulus is employed at the proximal end 58 of the sleeve element 16, this annulus will be of dimensions sufficient to cover an annular space 68, shown in FIG. 2, between the proximal end 58 of the sleeve element 16 and the annulus 38.

The annulus 62 may be joined to the guidewire 12 in at least two ways. As shown in FIG. 5, the proximal end 64 of the annulus 62 may be fixedly attached to the distal end 60 of the sleeve element 16 by means 37. The means 37 is preferably directed to form a sloped surface 70 connecting the proximal end 64 of the annulus 62 to the outer diameter surface of the sleeve element 16. The means 37 prevents fluid flow through the gap between the sleeve element 16 and the annulus 62 into the space 66, and the sloped surface 70 provides a substantially smooth transition from the outer diameter surface of the annulus 62 to the outer diameter surface of the sleeve element 16, thereby improving navigability of the guidewire 12. Because, in the illustrated embodiment, the sleeve element 16 and the annulus 62 are joined together and are not otherwise connected to the core wire 14, both are capable of conjoint rotation independent of the core wire 14.

An alternative method of attaching the annulus 62 to the guidewire 12 involves joining a distal end 72 of the annulus 62 to the annulus 40 adjacent the coil engaging surface 48 by means 37. By this method, the annulus 62 does not rotate conjointly with the sleeve element 16, but, because there is no connection between the sleeve element 16 and the annulus 62, resultant force applied to the sleeve element 16 is not transmitted to, and does not effect movement of the core wire 14. Irrespective of the method of annulus 62 attachment, the sleeve element 16 functions as described hereinabove, and the distal end 10 has a substantially smooth outer surface profile, thereby improving navigability of the guidewire 12. To further improve navigability, the outer surface of the distal end 10, including the sleeve member 16, the annuluses 38, 40, and 62, the coil 54 and the end tip 36, and/or of the entire length 22, can be coated with a lubricous substance, such as a hydrophilic coating, for giving that surface substantially constant lubricity.

Figures 6, 7:
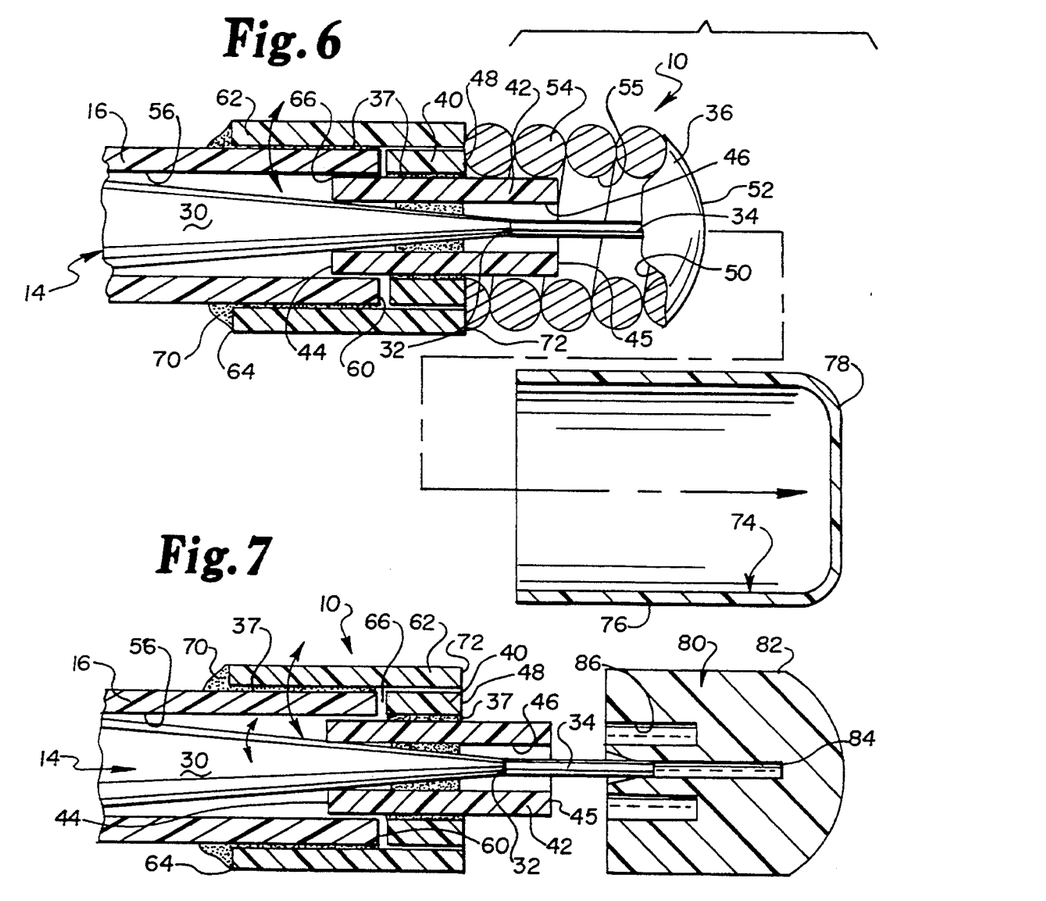
FIG. 6 is a view, similar to that of FIG. 5, of an additional embodiment of the invention having a coil contained within a sheath, exploded off for clarity.
FIG. 7 is a view, similar to that of FIG. 6, of a further embodiment of the invention wherein the coil is replaced by a polymeric body.

The embodiment of FIG. 6 is substantially similar to the embodiment shown in FIG. 5, hence the like reference numerals. However, to further improve navigability of the guidewire 12, the embodiment of FIG. 6 includes a separate sheath member 74 for covering an outer diameter surface 76 of the coil 54 and the rounded surface 52 of the end tip 36. By providing a separate sheath member 74, the coils comprising the coil 54 are not locked together as they may be in the prior art guidewires when coated or overmolded with a material, and accordingly, the coil 54 has a relatively wider range of flexibility.

The sheath member 74 comprises a polymeric material of high elasticity and low flexual modulus, such as polyurethane and the like, and is a hollow, substantially cylindrical body having a closed end 78. The sheath member 74 defines an inner diameter substantially equal to the outer diameter defined by the surface 76 of the coil 54, and the closed end 78 defines a configuration which complements a corresponding configuration of the rounded surface 52 of the end tip 36. The sheath member 74 may be attached to the coil 54 in a plurality of ways, viz. by adhesive, heat shrinking, and the like.

When the sheath member 74 is applied to the coil 54, the interior of the closed end 78 contacts the rounded surface 52 and the interior diameter surface of the sheath member 74 contacts the outer diameter surface 76 of the coil 54. Thus, there are two separate surfaces available at the far distal end of the guidewire 12. The outer diameter surface 76 provides flexibility useful in navigating the guidewire 12 through a lumen. The sheath member 74 has sufficient structural integrity for forming a substantially smooth exterior surface, and does not closely conform to the crests and troughs formed by adjacent coils of the coil 54, which also facilitates navigation of the guidewire 12. The substantially smooth exterior surface provided by the sheath member 74 eliminates crevices into which navigation-inhibiting fluid can flow and collect, and also eliminates the possibility that a portion of an interior surface of a lumen will be caught or pinched by adjacent coils of the coil 54. It is envisioned that the sheath member 74 can be utilized with a plurality of guidewire constructions.

Yet a further embodiment of the invention is shown in FIG. 7. In this embodiment, the coil 54 and the end tip 36 are eliminated and replaced by a flexible end body 80. The end body 80 has dimensions substantially equal to the corresponding dimensions of the coil 54 and the end tip 36, and may be formed from a suitable polymeric material, such a polyurethane and the like. The end body 80 has a substantially smooth outer surface 82 which provides similar navigability benefits as discussed earlier.

The end body 80 has a central bore 84 dimensioned for accepting a distal portion of the tapered segment 30 extending beyond the coil engaging surface 48 of the annulus 40 and the segment or ribbon 34, and an annular recess 86 for accepting a distal portion of the bearing 42 which also extends beyond the coil engaging surface 48 of the annulus 40. The exterior of the end body 80 may be fixed to the core wire 14 by means 37 or by other methods, such as by ultrasonic welding, various heat flow methods, and the like. The end body 80 may also be coated with a lubricous or hydrophilic substance, as discussed above, if desired.

The end body 80 is keyed onto the distal end 10 of the guidewire 12 so that movement or deformation of the core wire 14 causes corresponding movement or deformation of the end body 80. Because the core wire 14 extends through the end body 80 substantially similarly to the manner by which the core wire 14 extends through the coil 54, the end body 80 performs similarly to the coil 54. However, because the end body 80 has a substantially smooth outer surface 82 and is not comprised of coils, the end body 80 will not kink as the coil 54 might. Also, the end body 80 will not catch or pinch portions of the interior surface of the lumen as the coil 54 might. Just as differently configured coils 54 may be utilized with the invention, differently configured end bodies 80 may also be employed without departing from the scope of the present invention.

Figure 8:
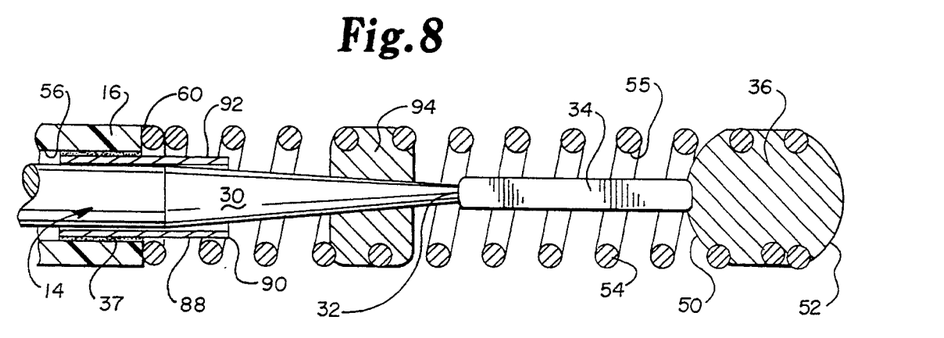
FIG. 8 is a view, similar to that of FIG. 4, illustrating another embodiment of the invention.

Yet another embodiment of the invention is illustrated in FIG. 8, employing an alternative method for retaining the sleeve element 16, and specifically the distal end 60 thereof, about the core 14. Here, the proximal end 58 of the sleeve element 16 is fixedly attached to the surface of the constant diameter segment 26 by adhesive means 37 in substantially the same way as it is in the embodiment of FIG. 4. The embodiment of FIG. 8, however, does not include a distal annulus 40, as the embodiment of FIG. 4 does. Instead, the sleeve element 16 extends the entire axial length from the smaller diameter end 24 of the tapered segment 18 to a position on the tapered segment 30.

At the distal end 60 of the sleeve element 16, the inner diameter surface 56 of the sleeve element 16 is fixedly attached to bridge means in the form of a cylinder 88, preferably in the form of a hypotube, which extends from the distal end 60 towards the proximal end 58 a certain, predetermined distance to insure a firm connection between the sleeve element 16 and the cylinder 88. It is to be noted that the cylinder 88 has an inner diameter larger than the outer diameter of the tapered segment 30 at adjacent points. The cylinder 88 is substantially similar to the bearing 42. Thus, the cylinder 88 does not come into contact with the tapered segment 30 or any other portion of the core 14 at any point. This insures that resultant force on the sleeve element 16 will not be transmitted to a distal portion of the core 14, thereby providing the guidewire 12 with increased navigability.

A distal end 90 of the cylinder 88 extends beyond the distal end 60 of the sleeve element 16 and into the coil 54 a certain distance sufficient to provide a smooth transition of flexibility from the sleeve element 16 to the coil 54. The cylinder 88 has an outer diameter substantially equal to the inner diameter of the coil 54. In this manner, an outer diameter surface 92 of the cylinder 88 supportively contacts the inner diameter surface 55 of the coil 54.

In the preferred construction, distal portions of the surface 92 of the cylinder 88 are fixedly attached to adjacent portions of the coil 54 by suitable means, such as solder and the like. In this manner, the cylinder 88 forms a bridge or juncture between the sleeve element 16 and the coil 54. Thus, resultant force applied to the sleeve element 16 can be transmitted through the cylinder 88 to a portion of the coil 54, but, because the distal end of the core 14 is not attached to the sleeve element 16, movement of the core 14, i.e. for intravascularly navigating the wire 12, is effectively decoupled from the forces on and movement of the sleeve element 16. Also, the dimensions of the coil 54 and the cylinder 88 are chosen such that the sleeve element 16 and the coil 54 present a substantially smooth, continuous outer surface profile for further improving navigation of the guidewire 12. This outer surface profile can also be coated with a lubricous substance, as discussed above.

Because resultant force on the sleeve element 16 can be transmitted to the cylinder 88 and the coil 54, a bead 94 of braze or solder, or like material, is provided on the coil 54 at a location between the distal end 90 of the cylinder 88 and the proximal portion 50 of the end tip 36, which can also be formed from similar braze or solder. The bead 94 extends along the outer diameter of the coil 54 at that location, and specifically forms a connection between the coil 54 and the tapered segment 30. It is to be noted that a length of the tapered segment 30, as well as the entire length of the ribbon or segment 34, and the coil 54 may extend beyond the distal end of the bead 94. This length is sufficient for deforming that portion into a predetermined configuration, such as a "J," thereby insuring increased intravascular navigability of the guidewire 12.

Specifically, the bead 94 provides a bearing point for any forces present on the sleeve element 16 and/or the coil 54. If a torque, or other resultant force, is applied to the sleeve element 16, that torque can be transmitted to the cylinder 88 and from there to the coil 54. However, the bead 94 does not allow the torque to be transmitted to portions of the coil 54 and the core 14 located distally of the bead 94. The bead 94 causes the torque to act upon the sleeve element 16, the cylinder 88 and the portion of the coil 54 between the distal end 60 of the sleeve element 16 and the proximal end of the bead 94. That portion of the coil 54 may twist or otherwise torsionally deform, thereby absorbing the torque or resultant force. More importantly, it is to be carefully noted that the resultant force does not effect the portions of the core 14 or the coil 54 located distally of the bead 94. The end tip 36 is also unaffected. Therefore, this embodiment of the invention also provides substantial decoupling of guidewire 12 navigating rotational forces and guidewire 12 axial shifting forces.

Figure 9:
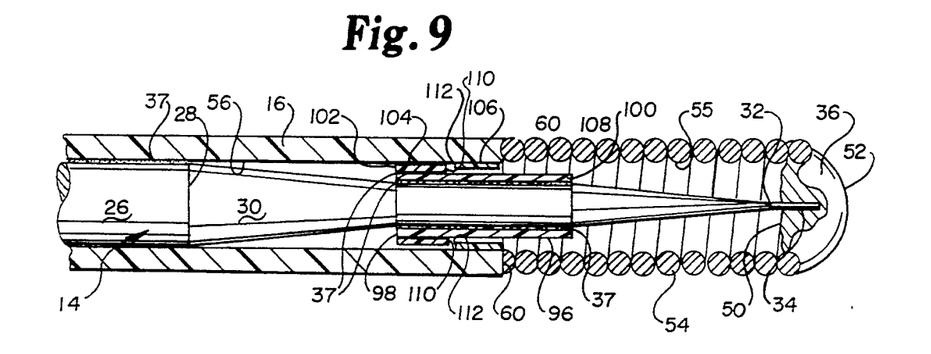
FIG. 9 is a view, similar to that of FIG. 8, showing an alternative construction of the invention.

The embodiment of the invention shown in FIG. 9 includes another construction of means for retaining or positively coupling the sleeve element 16 to the core wire 14. The proximal end 58 of the sleeve element 16 is fixedly attached to the segment 26 in the same manner as described hereinabove with respect to the embodiment of FIG. 8. The means for retaining the distal end 60 generally comprises a plurality of annuluses which cooperate to positively locate the sleeve element 16 about the core wire 14.

Specifically, a relatively elongate annulus 96, substantially similar to the bearing 42, is fixedly attached to a portion of the tapered segment 30 by a suitable amount of adhesive means 37, such that a proximal end 98 of the annulus 96 contacts the tapered surface of the segment 30. The proximal end 98 of the annulus 96 is located an axial distance proximally from the distal end 60 of the sleeve element 16 on the order of twice the axial length of the annulus 96. A distal end 100 of the annulus 96 projects into the interior of the coil 54 to provide a smooth flexibility transition from the sleeve element 16 to the coil 54.

An inner diameter surface of another annulus 102 is fixedly attached to the outer diameter surface of the annulus 96 adjacent the proximal end 98 by suitable means 37 such that the proximal end 98 of the annulus 96 is aligned with the proximal end of the annulus 102. The annulus 102 has an inner diameter slightly larger than an outer diameter of the annulus 96, but the axial length of the annulus 96 is larger than the axial length of the annulus 102. The annulus 102 has an outer diameter smaller than the inner diameter defined by the sleeve element 16. Thus, an outer diameter surface 104 of the annulus 102 can contact the inner diameter surface 56 of the sleeve element 16, and can act, in suitable circumstances, as a bearing surface for rotatably supporting the sleeve element 16. However, it is to be noted that there is no connection between the annulus 102 and the sleeve element 16, thereby insuring proper decoupling, as discussed above.

Another annulus 106 is fixedly attached to the inner diameter surface 56 of the sleeve element 16 adjacent the distal end 60 of the sleeve element 16 by suitable means 37 such that a distal end 108 of the annulus 106 is aligned with the distal end 60 of the sleeve element 16. The annulus 106 has an outer diameter substantially equal to the inner diameter of the sleeve element 16, and has an inner diameter somewhat smaller than the outer diameter of the annulus 102. The axial length of the annulus 106 is substantially the same as the axial length of the annulus 102. Thus, when assembled, a distal end 110 of the annulus 102 opposes a proximal end 112 of the annulus 106. Contact between the opposing ends 110 and 112 of the annuluses 102 and 106, respectively, positively locates and retains the sleeve element 16 with respect to the core wire 14.

In addition, while in the illustrated embodiment the distal end 108 of the annulus 106 is aligned with the distal end 60 of the sleeve element 16, it is envisioned that the distal end 108 may be located distally of the distal end 60. This construction would extend the annulus 106 into the interior of the coil 54 so that the interior diameter surface 55 of the coil 54 can engage an outer diameter surface of the annulus 106. The annulus 106 can, in addition to the annulus 96, provide a smooth transition of flexibility from the sleeve element 16 to the coil 54, while the coil 54 and the sleeve element 16 present a substantially smooth external surface profile which can be coated with a lubricous substance, as detailed hereinabove.

Figure 10:
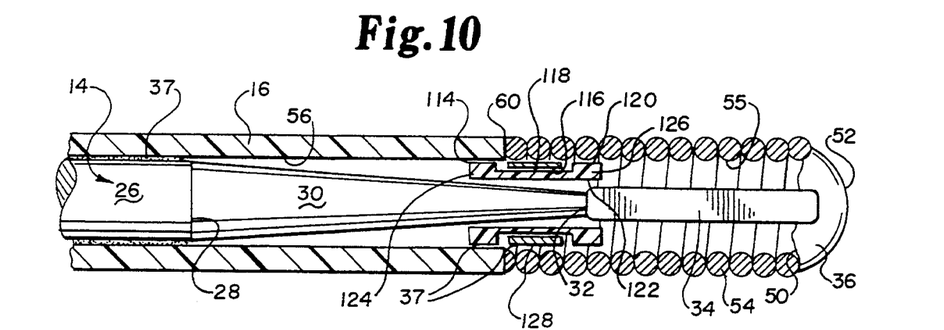
FIG. 10 is a view, similar to that of FIG. 5, showing means for positively limiting axial movement of a sleeve element with respect to a core wire.

An additional embodiment of the invention is shown in FIG. 10. This embodiment employs an alternative construction of the means for positively locating the distal end 60 of the sleeve element 16 with respect to the core wire 14. This construction of the means comprises a novelly constructed annulus 114 and a cylinder 116. The annulus 114 and the cylinder 116 are interengageable for positively coupling the sleeve element 16 to the core wire 14 such that the sleeve element 16 and the core 14 move substantially conjointly axially within a vascular lumen.

The annulus 114 is substantially cylindrical in configuration, however, the annulus 114 has an annular trough or recess 118 which extends from an outer diameter surface 120 of the annulus 114 radially inwardly towards an inner diameter surface 122 thereof. The recess 118 is disposed substantially axially centrally on the annulus 114, thereby forming a proximal projecting member 124 and a distal projecting member 126 on appropriate sides of the recess 118.

The surface 120 defines a diameter substantially equal to an inner diameter of the sleeve element 16, while the surface 122 defines a diameter larger than a diameter defined by any adjacent portion of the tapered segment 30. Thus, there is no connection between the annulus 114 and the core wire 14, however, in still alternative embodiments of this construction, contact between the inner diameter surface 122 and the core wire 14 may occur, but this does not effect intravascular navigability of the guidewire 12. The outer diameter surface 120 on the proximal projecting member 124 is attached to the inner diameter surface 56 of the sleeve element 16 by means 37 at a location adjacent the distal end 60 of the sleeve element 16. In this manner, a portion of the recess 118 and the distal projecting member 126 extend beyond the distal end 60 and into the interior of the coil 54.

The cylinder 116 can be a suitable hypotube, like the bearing 42, having an outer diameter substantially equal to the inner diameter of the coil 54. An outer diameter surface 128 of the cylinder 116 engages the inner diameter surface 55 of the coil 54, and is attached thereto in a suitable manner, such as by solder and the like. The cylinder 116 has an axial length smaller than the axial dimension of the recess 118, and has an inner diameter larger than a diameter defined by the surface of the recess 118.

The cylinder 116 is mounted to the inner diameter surface 55 of the coil 54 adjacent the proximal end thereof such that the cylinder 116 resides within the recess 118, the dimensions of the cylinder 116 and the recess 118 being chosen so that rotation of the annulus 114, induced by resultant force acting upon the sleeve element 16, will not cause rotation of the cylinder 116. However, the dimensions of the cylinder 116 and the recess 118 are such that axial movement of the sleeve element 16 is limited by engagement of opposite ends of the cylinder 116 with either the proximal projecting member 124 or the distal projecting member 126. The annulus 114 and the cylinder 116 cooperate to provide a smooth transition of flexibility from the sleeve element 16 to the coil 54. In addition, it is envisioned that the outer diameter surface 120 on the distal projecting member 126 may also be attached to the inner diameter surface 56 of the coil 54 if desired.

Figure 11:
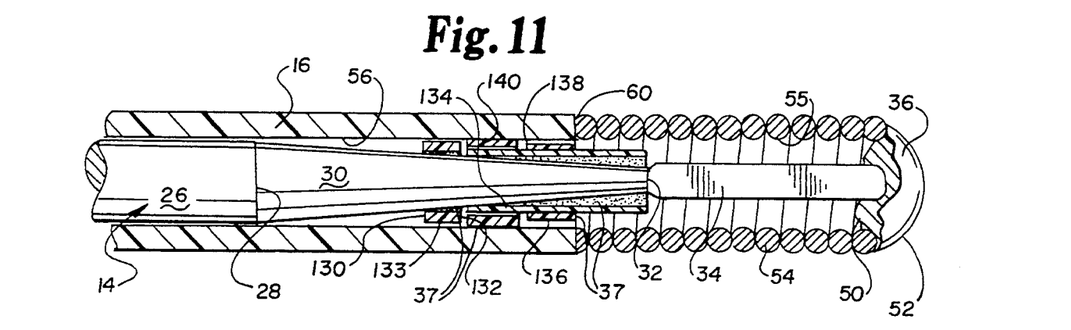
FIG. 11 is a view, similar to that of FIG. 10, illustrating another embodiment of the invention which also positively limits axial movement of the sleeve element with respect to a core wire.

Still another construction of the means for positively coupling the sleeve element 16 to the core wire 14 is illustrated in FIG. 11. This construction includes a plurality of annuluses cooperating with a cylinder 130. Specifically, the cylinder 130 is fixedly attached to the surface of the tapered segment 30 by means 37 at a position locating a distal end 132 of the cylinder 130 proximally offset from the distal end 60 of the sleeve element 16. The cylinder 130 is preferably a hypotube, similar to the bearing 42, having an outer diameter smaller than an inner diameter of the sleeve element 16. Thus, an outer diameter surface 133 of the cylinder 130 can act as a bearing surface for rotatably supporting the sleeve element 16.

In the illustrated embodiment, three annuluses are used. A first, relatively elongate annulus 134 is fixedly attached by means 37 to the tapered segment 30 such that a proximal end thereof is adjacent the distal end 132 of the cylinder 130. The annulus 134 has an outer diameter smaller than the outer diameter of the cylinder 130, and has an axial length sufficient for locating a distal end thereof distally of the distal end 60 of the sleeve element 16. A second annulus 136 is attached by means 37 to the first annulus 134 such that a distal end of the second annulus 136 substantially aligns with the distal end 60 of the sleeve element 16. The axial dimension of the second annulus 136 is smaller than the axial dimension of the annulus 134 such that a gap is formed between the proximal end 138 of the annulus 136 and the distal end of the cylinder 130. The gap is located at a position proximally offset from the distal end 60 of the sleeve element 16. The second annulus 136 defines an outer diameter similar to the outer diameter of the cylinder 130.

A third annulus 140 is attached by means 37 to the inner diameter surface 56 of the sleeve element 16 at a position offset proximally from the distal end 60 of the sleeve element 16. The third annulus 140 has an outer diameter substantially equal to an inner diameter of the sleeve element 16, and an inner diameter smaller than the outer diameters of the cylinder 130 and the annulus 136. The annulus 140 has an axial length smaller than the axial distance between the distal end 132 of the cylinder 130 and the proximal end 138 of the annulus 136.

The annulus 140 is located on the inner diameter surface 56 of the sleeve element 16 so that the annulus 140 is positioned within the gap between the proximal end 138 of the annulus 136 and the distal end 132 of the cylinder 130. There is no connection between the annulus 140 and the core wire 14. Thus, the sleeve element 16 and the annulus 140 are free to rotate substantially independently of the core wire 14. This insures the desired decoupling described above. In addition, a proximal end of the annulus 140 opposes the distal end 132 of the cylinder 130 and the distal end of the annulus 140 opposes the proximal end 138 of the annulus 136. In this manner, rotatable contact between the cylinder 130 and the annulus 140, and/or between the annulus 136 and the annulus 140 positively locates the sleeve element 16 about the core 14, and maintains the sleeve element 16 in appropriate position with respect to the core 14.

Figure 12:
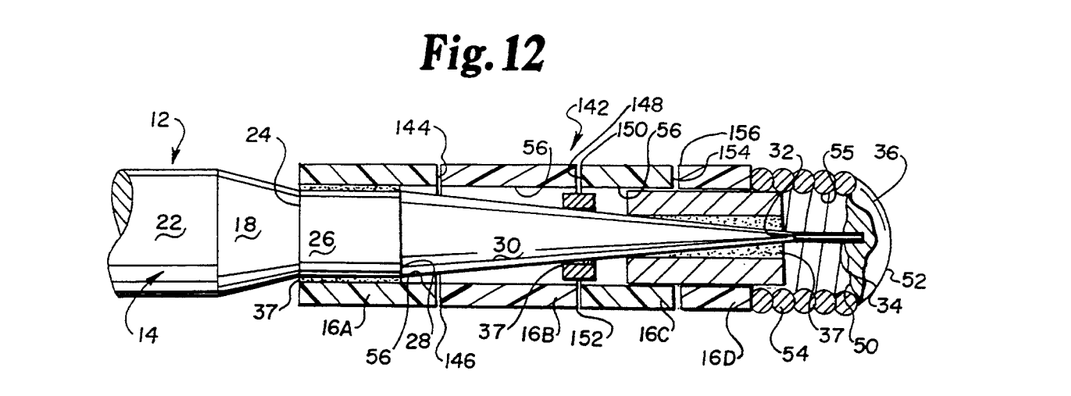
FIG. 12 is a view, similar to that of FIG. 2, showing yet another embodiment of the invention having multiple sleeve elements on a single core wire.

Yet another embodiment 142 of the invention is illustrated in FIG. 12. This embodiment 142 is substantially similar to the previous embodiments, hence the like reference characters, but employs a plurality of sleeve elements 16A, 16B, 16C and 16D aligned axially end-to-end on a single core wire 14. While only four sleeve elements 16A-16D are shown on the core wire 14, it is to be noted that a greater or lesser number of sleeve elements 16A-16D can be provided without departing from the scope of the present invention. Each of the sleeve elements 16A-16D functions independently substantially similarly to the sleeve element 16 discussed herein. The illustrated preferred construction of the embodiment 142 is substantially similar to the embodiment illustrated in FIG. 2, except for the differences to be noted in the following paragraphs.

Specifically, the sleeve element 16A of the embodiment 142 has a proximal end thereof fixedly attached to the segment 26 by a suitable amount of adhesive means 37, but a distal end 144 of the sleeve element 16A is not attached to the core wire 14, thereby allowing the core wire 14 to move substantially independently of the distal end 144 of the sleeve element 16A. It is to be noted that the axial lengths of the sleeve elements 16A–16D can be predetermined for providing greater degrees of motion independent of the core wire 14 and the sleeve elements 16A–16D, i.e. by providing a greater axial distance between a fixed proximal end and a free distal end of the sleeve elements 16A–16D, where appropriate.

The distal end 144 of the sleeve element 16A opposes a proximal end 146 of the sleeve element 16B. The sleeve element 16B is not attached to the core wire 14 or to any of the other sleeve elements 16A, 16C or 16D thereby allowing the sleeve element 16B to move or rotate substantially independently of the other components of the embodiment 142. A distal end 148 of the sleeve element 16B opposes a proximal end 150 of the sleeve element 16C. The sleeve element 16C is also not connected to any other component of the embodiment 142. This means that the sleeve elements 16B and 16C can rotate separately and in opposite directions simultaneously, independent of the core wire 14 as well as independent of each other, thereby shielding the core wire 14 from the resultant forces on the embodiment 142. The expanded independent rotatability of the sleeve elements 16B and 16C can provide the embodiment 142 with unique intravascular navigability characteristics which may facilitate intravascular treatment procedures, and may make some heretofore inaccessible treatment sites accessible.

Because the sleeve elements 16B and 16C are not attached to the core wire 14, or to any other components of the embodiment 142, a bearing 152, substantially similar to the bearing 42, may be provided for rotatably supporting the distal end 148 of the sleeve element 16B and the proximal end 150 of the sleeve element 16C. The axial length of the bearing 152 is long enough to provide support to the sleeve elements 16A–16D, but is small enough so as to not adversely effect core wire 14 navigability. The bearing 152 can prevent direct contact between the core wire 14 and the distal end 148 or the proximal end 150.

The sleeve element 16D is fixedly attached to the bearing 42 by adhesive means 37 in much the same manner as the distal annulus 40 is in the embodiments of FIGS. 2 and 4. However, the axial length of the sleeve element 16D may be chosen such that a proximal end 156 of the sleeve element 16D is located proximally of the proximal end 44 of the bearing 42. If this is the case, another bearing 152 may be provided to support the distal end 154 of the sleeve element 16C and the proximal end 156 of the sleeve element 16D.

It is to be noted that the axial lengths of the sleeve elements 16A–16D may be chosen such that the proximal end 146 of the sleeve element 16B is rotatably supported by the outer diameter bearing surface 41 of the segment 26, and such that a distal end 154 of the sleeve element 16C is rotatably supported by the bearing 42 in much the same way as the distal end 60 of the sleeve element 16 is supported by the bearing 42 in the embodiments of FIGS. 2 and 4. In addition, if desired, a suitable bearing 152 may be provided at any unsupported gap between two adjacent sleeve elements 16A–16D, but this may depend on the number and dimensions thereof.

Figure 13:
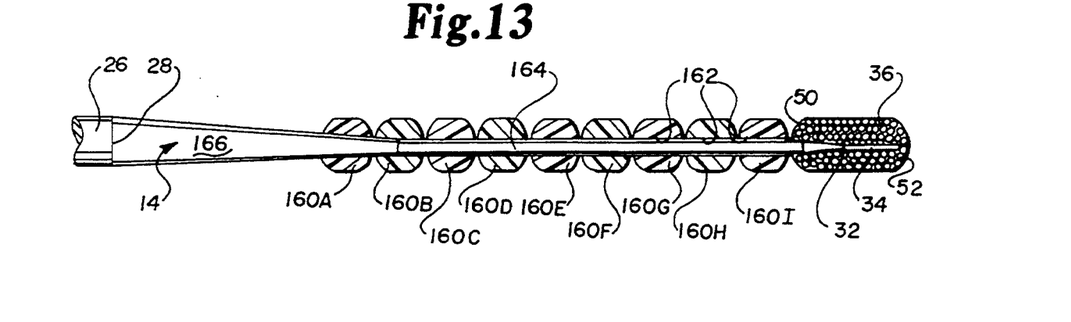
FIG. 13 is a view, similar to that of FIG. 12, showing a further embodiment of the invention having multiple elements.

Still another embodiment 158 of the invention is illustrated in FIG. 13. The embodiment 158 is substantially similar to the embodiment 142, and includes a novel construction of the means for increasing the navigability of the guidewire 12 in the form of a plurality of sleeve elements or beads 160A–160I surrounding a distal end 10 of the core wire 14. The precise number of beads 160A–160I employed in a given guidewire 12 construction may be larger or smaller depending upon the particular needs to be met by the guidewire 12. The beads 160A–160I are composed of the same materials as the other embodiments of the means for increasing navigability of the guidewire 12. The beads 160A–160I have a substantially spherical configuration and each has a through bore 162 extending across a diameter of the beads 160A–160I. The outer diameter of the beads 160A–160I is chosen such that a smooth outer surface profile is presented, as discussed above, and the diameter of the through bore 162 is chosen so that the beads 160A–160I are capable of rotation independent of each other as well as the core wire 14.

In the illustrated embodiment, the beads 160A–160I are disposed substantially along a relatively elongate constant diameter segment 164 of the core wire 14, however, it is to be noted that the beads 160A–160I, or a number thereof, may be positioned at various locations along the core wire 14 if an appropriate diameter of the bore 162 is chosen for a particular bead 160A–160I. The diameter of the bore 162 may be different for different beads 160A–160I.

As shown, the proximal-most bead 160A is disposed on a tapered segment 166 of the core wire 14. The gradually increasing diameter of the tapered segment 166, combined with the constant diameter of the through bore 162 allows the bead 160A to be force-fitted onto the core wire 14, and thus to act as a proximal retaining or coupling member for the plurality of beads 160A–160I. A coil 54, or other distal end tip construction, acts as a distal retaining member for the plurality of the beads 160A–160I. However, other constructions of proximal and distal retaining members are possible, especially if it is desirable to locate sets of beads 160A–160I at various locations along the axial length of the core wire 14. The axial spacing between adjacent beads 160A–160I can vary as desired, but it is to be fully appreciated that the beads 160A–160I rotate independent of each other and independent of the core wire 14, thereby shielding the core wire 14 from resultant force and increasing the navigability of the guidewire 12.

Further illustrating the structure and benefits of the present invention by example, a physician inserts the distal end 10 of the guidewire 12 into a patient's vascular system through a suitable access, such as an incision, slit or puncture. It is to be noted that, while this example relates directly to use of the guidewire 12 within a patient's vascular system, the same novel method can be employed when using the guidewire 12 within a catheter lumen. As the physician feeds the length 22 of the guidewire 12 into the vascular system, the distal end 10 encounters a curve or bend in an associated vessel or lumen. For the purposes of clarity, the navigation of the guidewire 12 will be discussed with respect to only one sleeve element 16 disposed on the core wire 14, but it is to be clearly understood that the same method applies equally and individually to multiple sleeve elements 16A–16D and beads 160A–160I.

As the distal end 10 approaches the curve in the vascular lumen, the sleeve element 16 comes into contact with the interior surface of the vessel, thereby generating a resultant force on the guidewire 12. Similar forces can be generated by contact between the sleeve element 16 and an interior surface of a catheter lumen, and can also be encountered when the physician attempts to select a desired branch lumen.

As the physician attempts to navigate the distal end 10 around the curve, the physician applies forces to the proximal end of the guidewire 12. This navigation may be particularly difficult if the curve or bend is relatively sharp. With the prior art guidewires, the forces required to rotate and to navigate the distal end of the guidewire would have to be of sufficient magnitude to overcome the influence of the resultant forces applied to the distal end by the contact with the interior surface of the vessel. However, with the present invention, the forces applied to the distal end 10 are reduced by the shielding provided by the sleeve element 16. If the distal end 10 is preformed, as described hereinabove, the treating physician will have to rotate the guidewire 12 to direct the distal end of the "J" around the bend. Similar procedures have to be performed to select a desired branch lumen, when encountered.

The resultant forces generated by contact between the distal end 10 and the interior surface of the vessel are applied to the sleeve element 16, which, in the embodiment of FIGS. 2, 5 and 6, can move substantially independently of the core wire 14. In the embodiment of FIGS. 4, 8, 9, 10 and 11, the forces applied to the sleeve element 16 are transmitted to a relatively proximal portion of the core wire 14, thereby leaving the relatively distal portion of the core wire 14 substantially free to move for directing the distal end 10 around the curve. The sleeve element 16 shields the distal end 10 of the guidewire 12 from the navigation-inhibiting effects of the resultant forces generated by contact between the guidewire 12 and the vessel.

The forces applied by the physician to the proximal end of the guidewire 12 do not have to overcome the resultant forces, thereby giving the distal end 10, and the guidewire 12 as a whole, an increased navigability as compared to the navigability of the prior art guidewires. Thus, the distal end 10 is more responsive to the proximally applied forces. Because the sleeve element 16 effectively shields the distal end 10 from contact-generated forces, the forces required for axial advancement of the guidewire 12 within the vessel are effectively decoupled from or independent of the forces, viz. rotational forces, required to navigate the guidewire 12, thereby giving the physician greater control over the guidewire 12 because the rotational forces can be applied substantially independently of the axial forces. The axial forces applied to the proximal end of the guidewire 12 cause axial shifting of the sleeve element 16 as well as the remainder of the guidewire 12 within a lumen. But, rotational forces applied to the proximal end do not cause rotation of the sleeve element 16, but cause rotation of the core wire 14 substantially independent of the sleeve element 16. This defines the decoupling of axial movements from rotational movements. Accordingly, if the physician encounters guidewire 12 navigation difficulties, the physician may wish to bring the sleeve element 16 into contact with the interior surface of the vessel or lumen to facilitate navigation of the guidewire 12. The shielding provided by the sleeve element 16 gives the guidewire 12 an increased ability to select, and discussed hereinabove, branch lumens in a patients's vascular system, as compared to some prior art guidewires.

Because the distal end 10 of the guidewire 12 has a substantially smooth outer surface profile, advancement of the guidewire 12 within the vessel is substantially uninhibited by the structure of the guidewire. No spaces are available into which navigation-inhibiting fluids, such as blood and the like, can flow and coagulate, as discussed above. Absence of such spaces also reduces the probability that a portion of the interior surface of the vessel may be caught or pinched by the guidewire 12. Utilization of the sheath member 74 or the end body 80 can further reduce this probability while also cooperating with the remainder of the distal end 10 to present a substantially smooth, continuous outer surface profile. Because the outer surface profile is substantially smooth and continuous, the lubricity of that surface, and thus of the distal end 10, can be substantially constant throughout the length thereof.

In the preferred, best mode embodiment of the invention, it has been determined that the following materials are desirable. This listing of materials is intended for illustration only, and is not intended to limit the scope of the invention. The sleeve elements 16, 16A–16D, the beads 160A–160I and the annuluses 38, 40, 62, 96, 102, 106, 114, 134, 136, and 140 are formed from a suitable polymeric material, such as polyimides, polyamides, polyethylenes, suitable polyesters and polyethers, a fluoropolymer, such as TEFLON®, polyphenylene sulfide, polysulfones, polyetherimides, polyetherether ketones, liquid crystal polymers, and the like, having sufficient structural rigidity and resistance to compression and expansion. The bearing 42 and the cylinders 88, 116, and 130 may also be polyimide, suitable polyesters and polyethers, a fluoropolymer, such as TEFLON®, or may be a stainless steel hypotube. It has been determined that polyimide is the preferred material for the sleeve element 16, the annuluses 38, 40, 62, 96, 102, 106, 114, 134, 136 and 140 and the bearing 42.

The means 37 comprises an appropriate amount of a suitable adhesive, such as a cyanoacrylate, an epoxy and the like, however, if greater flexibility of the means 37 is desired, a polyurethane may be used, thereby allowing greater flexibility of the distal end 10 of the guidewire 12. The core wire 14 can be of any suitable material, such as stainless steel, nitinol, and the like, while the coil 54 and/or the end tip 36 can be formed from a radiopaque material, such as platinum, tungsten, tantalum, or gold, for example, thereby allowing the physician to monitor progression of the distal end 10 through the patient's vascular system by radiography or similar imaging technique. The sheath 74 and the end body 80 comprise an elastomer or other polymeric material having low flexural modulus and high elasticity, such as polyimide, polyurethane, suitable polyesters, polyethers, and polyethylenes, and the like. The lubricous coating can be silicone, or a hydrophilic material, especially polyvinylpyrrolidone, polyacrylamide, polyethylene oxide, and the like.

In the current best mode embodiment of the invention, the following dimensions are used. However, these dimensions are for illustrative purposes only, and may vary depending upon particular application of the invention. The guidewire 12 has an axial length within the range of 200 cm, but this length is dependent upon the vascular distance from the insertion site to the treatment site. The length 22 has an outer diameter measuring approximately 0.36 mm to 0.41 mm. The axial length from the smaller diameter end 24 to the rounded surface 52 of the end tip 36 is between 30 to 40 cm. The tapered segment 18 has an axial length of approximately 5.0 cm to 7.6 cm. The length of the tapered segment 18 is chosen to provide a smooth transition of flexibility from the length 22 to the distal end 10. The constant diameter segment 26 has an axial length of approximately 2.5 cm, the tapered segment 30 has an axial length within the range of 20 cm to 50 cm, and the segment 34 has an axial length within the range of 2 cm to 5 cm. It is to be noted that the length of the tapered segment 30 and the segment or ribbon 34 may vary depending upon the particular application of the guidewire 12, viz. if it is desired to bend the segments 30 and 34, or portions thereof, into an arcuate configuration, such as a "J"-shape, for increasing navigability of the guidewire 12.

The sleeve element 16 is substantially cylindrical having an outer diameter of 0.33 mm and an axial length of 20 cm to 50 cm. The sleeve element 16 has a thickness of only 0.026 mm, thereby insuring that the sleeve element 16 will not interfere with the flexibility or rotation of the core wire 14. The annuluses 38 and 40 have inner and outer diameters equal to the corresponding diameters of the sleeve element 16 to insure a smooth outer surface profile, but, the annuluses 38 and 40 have axial lengths of only 0.32 cm. Because the annuluses 38 and 40 have such reduced axial lengths as compared to the axial length of the sleeve element 16, the annuluses 38 and 40 do not interfere with the flexibility or rotation of the core wire 14, even though the annuluses 38 and 40 are attached to the core wire 14.

The annular spaces 66 and 68 between the annuluses 38 and 40 and the sleeve element 16 have axial lengths within the range of 0.13 mm to 3 mm. This axial dimension of the spaces 66 and 68 need only be large enough to allow for independent movement of the sleeve element 16 and to allow for flexibility of the distal portion of the core wire 14, as discussed hereinabove, and is dependent upon application of the guidewire 12.

The bearing 42 is substantially cylindrical having inner and outer diameters chosen to provide a bearing surface 41 for the sleeve element 16 and also to insure that the flexibility of the tapered segment 30 is not reduced. Preferably, the bearing 42 has an inner diameter of 0.15 mm, an outer diameter of 0.23 mm, a thickness of 0.076 mm, and a length of 3.18 mm. To further facilitate independent movement of the sleeve element 16, a radial gap measuring within the range of 0.01 mm to 0.03 mm is provided between the inner diameter surface 56 of the sleeve element 16 and the outer diameter surface of the bearing 42.

The distal end 45 of the bearing 42 extends axially within the coil 54 and engages the inner diameter surface 55 thereof along an axial distance of approximately 0.15 mm to 0.23 mm extending from the coil engaging surface 48 of the annulus 40. This length is sufficient to provide a smooth, continuous transition of flexibility from the portion of the core wire 14 adjacent the annulus 40 to the portion of the core wire 14 adjacent the coil 54. The coil 54 has an outer diameter of 0.33 mm, and inner diameter of 0.05 mm, and a pitch of 0.10 mm.

The annulus 62 is also cylindrical having an axial length of approximately 0.64 cm, which is sufficient to cover the annular spaces 66 and 68, which, at the most, have axial lengths of 3 mm. The inner diameter and the outer diameter of the annulus 62 is chosen such that the annulus 62 has a thickness of approximately 0.01 mm. In this manner, the substantially smooth outer surface profile of the distal end 10 is preserved.

In the embodiment of FIG. 6, the sheath 74 has an axial length and an outer diameter equal to the corresponding dimensions of the coil 54. Because a plurality of different coil 54 configurations can be used with the invention, a corresponding number of different sheaths 74 can also be employed. The same is true of the end body 80. However, most of the sheaths 74 have a thickness measuring within the range of 0.05 mm to 0.13 mm.

By providing the distal end 10 of the guidewire 12 with increased navigability, the sleeve element 16 of the present invention presents a distinct improvement in guidewire technology. Guidewires 12 employing sleeve elements 16, according to the teachings of the invention, can navigate narrow, tortuous passageways, such as vascular systems and the like, with greater ease than the prior art guidewires because the distal ends 10 thereof are substantially shielded from the navigation-inhibiting effects of resultant forces by the sleeve element 16. Access to certain treatment sites is increased, as is vascular branch lumen selectability, and it is envisioned that appropriate utilization of the sleeve element 16 may make some heretofore inaccessible treatment sites accessible. A guidewire 12 with a sleeve member 16 can be particularly desirable in accessing, for instance, carotid vessels and vessels proximate soft tissues, intracranial vasculature or other complex or highly tortuous vasculature.

It is to be fully understood that, while the alternative embodiments of the invention are illustrated in separate Figures and are discussed in detail separately, the alternative embodiments of the invention, and the concepts or teachings thereof, can be successfully employed in a number of different combinations.

While preferred embodiments of the present invention are shown and described, it is envisioned that those skilled in the art may devise various modifications of the present invention without departing from the spirit and scope of the appended claims.

I claim:

1. A medical guidewire including a distal end for entering and navigating in a lumen, said distal end comprising:
    a core having a length for navigating the guidewire in the lumen;
    a formable distal tip included at the distal end of the core;
    a sleeve element substantially surrounding the core over less than a majority of the length of the core and being at least in part rotatable with respect to said core;
    the sleeve element being offset proximally of the formable distal tip such that said formable distal tip is movable independently of the sleeve element; and
    the sleeve element being positively coupled to the core such that said sleeve element and said core move substantially conjointly axially within said lumen.

2. A medical guidewire as defined in claim 1 wherein the sleeve element comprises a polymeric material.

3. A medical guidewire as defined in claim 1 wherein the sleeve element comprises a hollow cylinder; and wherein the core extends through the cylinder such that the cylinder can rotate substantially independently of and with respect to the core and such that the formable distal tip can move independently of the sleeve element.

4. A medical guidewire as defined in claim 1 wherein the sleeve element has a proximal end and a distal end; wherein the core comprises a relatively proximal portion and a relatively distal portion both offset proximally of the formable distal tip; and wherein the proximal end of said sleeve element is attached to the relatively proximal portion of said core such that the relatively distal portion of said core can move substantially independently of and with respect to said distal end of said sleeve element.

5. A medical guidewire as defined in claim 1 wherein the sleeve element has a distal end; wherein a portion of the core extends through the sleeve element and beyond the distal end of the sleeve element; further comprising a coil defining an inner diameter surface substantially surrounding the portion; and further comprising a tube attached to the core and contacting the inner diameter surface for providing a smooth flexibility transition from said sleeve element to said coil.

6. A medical guidewire as defined in claim 1 further comprising means for positively coupling the sleeve element about the core.

7. An improvement for facilitating navigability of an intravascular device in a lumen, said intravascular device having a distal end insertable into the lumen, the distal end including a core for navigating the intravascular device in the lumen, the core having an axial length, said improvement comprising:
  a sleeve element separate from and disposed substantially around the core;
  the sleeve element extending over less than a majority of the axial length; and
  the sleeve element being at least in part rotatable with respect to said core.

8. An improvement as defined in claim 7 wherein the sleeve element comprises a hollow cylinder; wherein the core has a distal end; further comprising a formable distal tip included at the distal end of the core; and wherein the core extends through the cylinder such that the distal tip extends distally of the cylinder so that the distal tip moves independently of the cylinder.

9. A guidewire insertable into a lumen, the guidewire comprising:
  a. a core having an axial length for navigating the guide wire within the lumen; and
  b. means for increasing the navigability of the guide wire, wherein the means for increasing navigability of the guidewire comprises a sleeve element disposed over less than a majority of the axial length of the core, said sleeve element further being moveable with respect to said core for increasing the navigability of the guidewire in the lumen.

10. A guidewire as defined in claim 9 wherein the sleeve element comprises a cylinder; and wherein the core is disposed through the sleeve element.

11. A guidewire as defined in claim 9 wherein the sleeve element has a proximal end and a distal end; and wherein the proximal end is attached to the core such that the core can move independently of the distal end.

12. A guidewire as defined in claim 9 wherein the core has a proximal end and a distal end; further comprising a coil substantially surrounding the core distally of the sleeve element; and further comprising bridge means for connecting the sleeve element to the coil.

13. A guidewire as defined in claim 12 wherein the bridge means comprises a hypotube.

14. A guidewire as defined in claim 12 wherein the sleeve element has an inner diameter surface and the coil has an inner diameter surface; and wherein the bridge means is operatively connected to the inner diameter surface of the sleeve element and to the inner diameter surface of the coil.

15. A guidewire as defined in claim 12 wherein the coil has a proximal end and the sleeve element has a distal end; wherein the proximal end of the coil opposes the distal end of the sleeve element; and further comprising an attachment connecting the coil to the core located distally of the proximal end of the coil.

16. A guidewire as defined in claim 15 wherein the attachment comprises at least one of solder and braze.

17. A guidewire as defined in claim 9 wherein the sleeve element has a proximal end; and wherein the proximal end is attached to the core.

18. A method of navigating a medical guidewire within a lumen having an interior surface comprising the steps of:
  providing a medical guidewire having a core for navigating the guidewire within the lumen, and a sleeve element substantially surrounding the core over less than a majority of an axial length thereof and being at least in part rotatable with respect to said core, the sleeve element being positively coupled to the core such that said sleeve element and said core move substantially conjointly axially within the lumen;
  engaging the sleeve element with the interior surface; and
  rotating the core with respect to said sleeve element for navigating the guidewire within said lumen.

19. A method of navigating a guidewire within a lumen comprising the steps of:
  providing a guidewire having a core having an axial length for navigating the guidewire within the lumen, and a sleeve element substantially surrounding the core over less than a majority of the axial length of the core and being moveable with respect to said core;
  applying a substantially axially directed force to the core for causing conjoint axial shifting of the core and the sleeve element within the lumen; and
  applying a substantially rotational force to the core for causing rotational movement of the core with respect to the sleeve element.

* * * * *